United States Patent
Stammer et al.

(10) Patent No.: US 11,097,202 B2
(45) Date of Patent: Aug. 24, 2021

(54) ENERGY RECOVERY IN A METHOD FOR PREPARING 1,3,5-TRIOXANE

(71) Applicants: BASF SE, Ludwigshafen am Rhein (DE); Kolon Plastics Inc., Gwacheon-si (KR)

(72) Inventors: Achim Stammer, Ludwigshafen am Rhein (DE); Thomas Heitz, Ludwigshafen am Rhein (DE); Marvin Kramp, Ludwigshafen am Rhein (DE); JongMoon Kim, Gimcheon (KR); In-Gi Cho, Gimcheon (KR); Jin-Sang Choi, Gimcheon (KR); Sang-Yup Lee, Gimcheon (KR)

(73) Assignees: BASF SE, Ludwigshafen am Rhein (DE); Kolon Plastics Inc., Gwacheon-Si (KR)

( * ) Notice: Subject to any disclaimer, the term of this patent is extended or adjusted under 35 U.S.C. 154(b) by 0 days.

(21) Appl. No.: 16/062,752

(22) PCT Filed: Dec. 7, 2016

(86) PCT No.: PCT/EP2016/080090
§ 371 (c)(1),
(2) Date: Jun. 15, 2018

(87) PCT Pub. No.: WO2017/102504
PCT Pub. Date: Jun. 22, 2017

(65) Prior Publication Data
US 2020/0261823 A1 Aug. 20, 2020

(30) Foreign Application Priority Data
Dec. 18, 2015 (EP) ..................................... 15201263

(51) Int. Cl.
*C07D 323/06* (2006.01)
*B01D 3/00* (2006.01)
*B01D 3/40* (2006.01)

(52) U.S. Cl.
CPC ............. *B01D 3/007* (2013.01); *B01D 3/009* (2013.01); *B01D 3/40* (2013.01); *C07D 323/06* (2013.01)

(58) Field of Classification Search
CPC ....... B01D 3/009; C07D 323/06; Y02P 20/10; Y02P 70/10
(Continued)

(56) References Cited

U.S. PATENT DOCUMENTS

| 4,720,557 A | * | 1/1988 | Erdman | .................... C10L 1/32 549/368 |
| 2016/0145390 A1 | | 5/2016 | Schmidt et al. | |

(Continued)

FOREIGN PATENT DOCUMENTS

| CN | 1993341 A | 7/2007 |
| CN | 103370313 A | 10/2013 |

(Continued)

OTHER PUBLICATIONS

International Search Report for PCT/EP2016/080090 dated Feb. 22, 2017.
(Continued)

*Primary Examiner* — Taylor V Oh
(74) *Attorney, Agent, or Firm* — Faegre Drinker Biddle & Reath LLP

(57) ABSTRACT

The present invention relates to a process for energy recovery in a process for the preparation of 1,3,5-trioxane.

15 Claims, 1 Drawing Sheet

(58) Field of Classification Search
USPC .......................................................... 549/368
See application file for complete search history.

(56) References Cited

U.S. PATENT DOCUMENTS

| | | |
|---|---|---|
| 2016/0340509 A1 | 11/2016 | Schmidt et al. |
| 2017/0081472 A1 | 3/2017 | Zhu et al. |
| 2018/0009944 A1 | 1/2018 | Gramlich et al. |
| 2018/0009950 A1 | 1/2018 | Gramlich et al. |

FOREIGN PATENT DOCUMENTS

| | | |
|---|---|---|
| EP | 2634182 A2 | 9/2013 |
| EP | 2634183 A2 | 9/2013 |
| WO | 2006/003003 A1 | 1/2006 |
| WO | WO-2011131609 A2 | 10/2011 |

OTHER PUBLICATIONS

Written Opinion of the International Searching Authority for PCT/EP2016/080090 dated Feb. 22, 2017.

\* cited by examiner

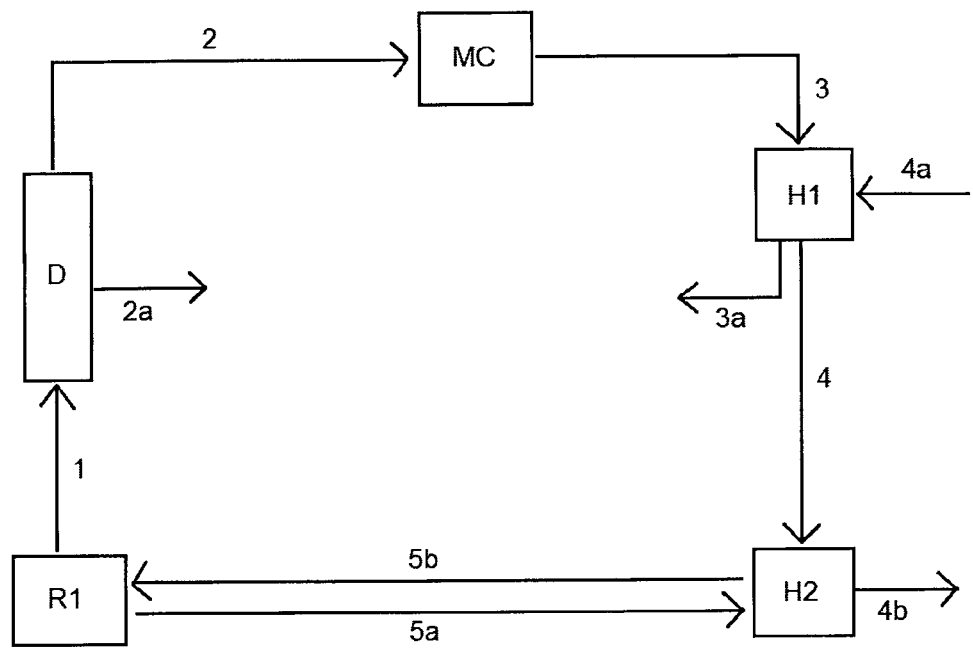

ENERGY RECOVERY IN A METHOD FOR PREPARING 1,3,5-TRIOXANE

CROSS-REFERENCE TO RELATED APPLICATIONS

This application is a national stage application (under 35 U.S.C. § 371) of PCT/EP2016/080090, filed Dec. 7, 2016, which claims benefit of European Application No. 15201263.9, filed Dec. 18, 2015, both of which are incorporated herein by reference in their entirety.

The present invention relates to a process for energy recovery in a process for the preparation of 1,3,5-trioxane.

1,3,5-trioxane is in general produced by trimerization of formaldehyde in the presence of water and a catalyst, in particular an acidic catalyst. The trimerization of formaldehyde and the separation of the desired 1,3,5-trioxane from the product mixture obtained during the trimerization is very energy-consuming and therefore costly. Usually, the product mixture obtained during the trimerization is transferred into a distillation and extraction or crystallization apparatus to separate the desired product 1,3,5-trioxane from the product mixture. There are several methods described in the state of the art to remove 1,3,5-trioxane from the product mixture.

EP 2 634 182 and EP 2 634 183 both describe a distillation unit and an extraction unit which are integrally formed into one distillation apparatus. In these processes, 1,3,5-trioxane is prepared from formaldehyde in a reactor. The obtained product mixture is transferred into the distillation apparatus. A stream comprising 1,3,5-trioxane is discharged from the distillation apparatus and, subsequently, this stream is separated into an oil phase and a water phase. The water phase is refluxed into the distillation apparatus. By the processes described in EP 2 634 182 and EP 2 634 183, the formation of byproducts in the distillation apparatus can be reduced. However, the method is still very energy-consuming as more than 3 tons of steam are necessary to purify 1 ton of 1,3,5-trioxane.

The object underlying the present invention is, therefore, to provide a process with which the energy consumption of a process for the preparation of 1,3,5-trioxane can be reduced with regard to processes described in the state of the art.

This object is achieved by a process for energy recovery in a process for the preparation of 1,3,5-trioxane comprising the steps a) reacting formaldehyde in the presence of water and at least one acidic catalyst in a first reactor (R1) to obtain a first product mixture (P1), which comprises water and 1,3,5-trioxane, wherein the first product mixture (P1) is transferred as stream (1) from the first reactor (R1) to a distillation tower (D), b) contacting the first product mixture (P1) with at least one extractant (E) in the distillation tower (D) to obtain an overhead product (OP), and a side cut (SC), wherein the overhead product (OP) comprises the at least one extractant (E) and water, and wherein the side cut (SC) comprises the at least one extractant (E) and 1,3,5-trioxane, wherein the overhead product (OP) is transferred as stream (2) from the distillation tower (D) to a mechanical compressor (MC), wherein the stream (2) has a first temperature (T1) and a first pressure (p1), c) mechanical compression of the stream (2) in the mechanical compressor (MC) to obtain a compressed stream (3), which has a second temperature (T2) and a second pressure (p2), wherein the second temperature (T2) of the compressed stream (3) is higher than the first temperature (T1) of the stream (2) and wherein the second pressure (p2) of the compressed stream (3) is higher than the first pressure (p1) of the stream (2), d) transferring heat from the compressed stream (3) to the first reactor (R1).

The inventive process makes it possible to recover energy from a process for the preparation of 1,3,5-trioxane and to re-use the recovered energy in the preparation of 1,3,5-trioxane. Therefore, by the inventive process, the total energy consumption of the process for the preparation of 1,3,5-trioxane can be significantly reduced, which makes the inventive process for the preparation of 1,3,5-trioxane very cost-efficient.

The inventive process will be described in more detail hereinafter.

Step a)

In step a), formaldehyde is reacted in the presence of water and at least one acidic catalyst in a first reactor (R1) to obtain a first product mixture (P1).

For example in the range from 30 to 70% by weight of formaldehyde is reacted in the presence of 30 to 70% by weight of water and from 0.1 to 15% by weight of the at least one acidic catalyst, based on the sum of the percentage by weight of formaldehyde, water and the at least one acidic catalyst.

Preferably, in the range from 40 to 65% by weight of formaldehyde is reacted in the presence of 35 to 60% by weight of water and from 0.1 to 10% by weight of the at least one acidic catalyst, based on the sum of the percentage by weight of formaldehyde, water and the at least one acidic catalyst.

Particularly preferred, in the range from 49 to 62% by weight of formaldehyde is reacted in the presence of 38 to 51% by weight of water and from 0.5 to 5% by weight of the at least one acidic catalyst, based on the sum of the percentage by weight of formaldehyde, water and the at least one acidic catalyst.

During the reaction of formaldehyde in the presence of water and the at least one acidic catalyst, the formaldehyde trimerizes to give 1,3,5-trioxane. This trimerization reaction is known to the skilled person and catalyzed by the at least one acidic catalyst. Moreover, byproducts may form during the reaction of formaldehyde. These byproducts are known to the skilled person and are for example methanol, methylformiate, dimethoxymethane, formic acid, tetroxane, and dimethoxydimethylether.

The reaction of formaldehyde is typically carried out at a temperature in the range from 80 to 120° C., preferably in the range from 90 to 115° C., and particularly preferred in the range from 95 to 110° C.

Therefore, the temperature in the first reactor (R1) during step a) is typically in the range from 80 to 120° C., preferably in the range from 90 to 115° C., and particularly preferred in the range from 95 to 110° C.

The reaction of the formaldehyde is usually carried out at a pressure in the range from 0.1 to 5 bara, preferably in the range from 0.5 to 3 bara, and particularly preferred in the range from 0.9 to 1.5 bara.

Therefore, the pressure in the first reactor (R1) during step a) is usually in the range from 0.1 to 5 bara, preferably in the range from 0.5 to 3 bara, and particularly preferred in the range from 0.9 to 1.5 bara. "bara" within the context of the present invention means the absolute pressure (bar absolute). The absolute pressure bara is 0-referenced against a perfect vacuum, using an absolute scale. Usually, bara is equal to a gauge pressure plus atmospheric pressure.

"At least one acidic catalyst" within the context of the present invention means precisely one acidic catalyst and also a mixture of two or more acidic catalysts.

As the at least one acidic catalyst, any acidic catalyst that catalyzes the reaction, preferably the trimerization, of formaldehyde in step a) is suitable.

The at least one acidic catalyst can be a homogeneous or a heterogeneous catalyst. Preferably, the catalyst is a homogeneous catalyst.

Particularly preferred as the at least one catalyst is sulfuric acid or methane sulfonic acid.

As first reactor (R1), any reactor known to the skilled person and which is suitable for the temperatures and the pressures of the reaction of formaldehyde can be used.

These reactors are known to the skilled person and are for example tank, pipe or tubular reactors, as for example batch reactors or continuous stirred-tank reactors.

Formaldehyde, water and the at least one acidic catalyst can be provided to the first reactor (R1) by any method known to the skilled person. Preferably, the formaldehyde is fed to the first reactor (R1) together with water and separately from the at least one acidic catalyst. Particularly preferred, formaldehyde together with water is fed continuously to the first reactor (R1) and separately from the at least one acidic catalyst, which is typically fed discontinuously to the first reactor (R1).

In step a), the first product mixture (P1) is obtained. The first product mixture (P1) comprises water and 1,3,5-trioxane. If byproducts are formed during the reaction of formaldehyde, they are as well comprised in the first product mixture (P1). Concerning the byproducts, the embodiments and preferences described above hold true.

Moreover, the first product mixture (P1) typically furthermore comprises unreacted formaldehyde.

The first product mixture (P1) is transferred as stream (1) from the first reactor (R1) to a distillation tower (D) in step a).

The stream (1) has the same composition as the first product mixture (P1). For example, the stream (1) comprises from 31 to 56% by weight of formaldehyde, from 8 to 32% by weight of 1,3,5-trioxane, from 11 to 35% by weight of water, and from 1 to 25% of byproducts, based on the sum of the percentage by weight of formaldehyde, trioxane, water and byproducts comprised in the stream (1), preferably based on the total weight of the stream (1).

Preferably, the stream (1) comprises from 36 to 51% by weight of formaldehyde, from 13 to 27% by weight of 1,3,5-trioxane, from 16 to 30% by weight of water, and from 6 to 20% by weight of byproducts, based on the sum of the percentage by weight of formaldehyde, trioxane, water and byproducts comprised in the stream (1), preferably based on the total weight of the stream (1).

Particularly preferred, the stream (1) comprises from 38 to 46% by weight of formaldehyde, from 18 to 22% by weight of trioxane, from 21 to 25% by weight of water, and from 11 to 15% by weight of byproducts, based on the sum of the percentage by weight of formaldehyde, trioxane, water and byproducts comprised in the stream (1), preferably based on the total weight of the stream (1).

Another object of the present invention is, therefore, a process wherein the stream (1) in step a) comprises from 31 to 56% by weight of formaldehyde, from 8 to 32% by weight of 1,3,5-trioxane, from 11 to 35% by weight of water and from 1 to 25% by weight of byproducts, based on the total weight of the stream (1).

The temperature of the stream (1) is usually in the range from 80 to 120° C., preferably in the range from 90 to 115° C., and particularly preferred in the range from 95 to 110° C.

The pressure of the stream (1) is usually in the range from 0.1 to 5 bara, preferably in the range from 0.5 to 3 bara, and particularly preferred in the range from 0.9 to 1.5 bara.

The first product mixture (P1) can be transferred as stream (1) from the first reactor (R1) to the distillation tower (D) by any method known to the skilled person. Typically, a pipe is used to transfer the stream (1) from the first reactor (R1) to the distillation tower (D).

As distillation tower (D), any distillation tower is suitable which allows the separation of 1,3,5-trioxane from the first product mixture (P1) by using at least one extractant (E) in step b).

Preferably, the distillation tower (D) comprises a distillation section and an extraction section. Particularly preferred, the distillation section and the extraction section are both comprised in the distillation tower (D). These distillation towers (D) are known to the skilled person and are for example described in WO 2011/131609.

Step b)

In step b), the first product mixture (P1) is contacted with at least one extractant (E) in the distillation tower (D) to obtain an overhead product (OP) and a side cut (SC).

"At least one extractant (E)" within the context of the present invention means precisely one extractant (E) and also a mixture of two or more extractants (E). Precisely one extractant (E) is preferred.

As the at least one extractant (E), any extractant known to the skilled person which makes it possible to separate the first product mixture (P1) into an overhead product (OP) and a side cut (SC) is suitable.

The at least one extractant (E) in step b) is preferably selected from the group consisting of benzene, 1,2-dichloroethane and methylene chloride.

Most preferably, the at least one extractant (E) in step b) consists of benzene.

Another object of the present invention is, therefore, a process wherein the at least one extractant (E) in step b) is selected from the group consisting of benzene, 1,2-dichloroethane and methylene chloride.

The first product mixture (P1) can be contacted with the at least one extractant (E) in the distillation tower (D) by any method known to the skilled person. Preferably, the first product mixture (P1) is contacted with the at least one extractant (E) in an extractive distillation section, which is comprised in the distillation tower (D).

The temperature at which the first product mixture (P1) is contacted with the at least one extractant (E) in the distillation tower (D) is typically in the range from 30 to 150° C., preferable in the range of 50 to 150° C., more preferably in the range from 60 to 130° C., and particularly preferred in the range from 65 to 105° C.

The pressure at which the first product mixture (P1) is contacted with the at least one extractant (E) is typically in the range from 0.1 to 5 bara, preferably in the range from 0.5 to 3 bara, and particularly preferred in the range from 0.9 to 1.5 bara.

During the contacting of the first product mixture (P1) with the at least one extractant (E) in step b), an overhead product (OP) and a side cut (SC) are obtained.

The overhead product (OP) comprises the at least one extractant (E) and water. The overhead product (OP) can, furthermore, comprise at least one of the byproducts that were comprised in the product mixture (P1), formaldehyde and a residual of 1,3,5-trioxane.

"A residual of 1,3,5-trioxane" within the context of the present invention means from 0.01 to 1% by weight, preferably from 0.5 to 0.8% by weight, and particularly preferable from 0.1 to 0.5% by weight of 1,3,5-trioxane, based on the total weight of the overhead product (OP).

The overhead product (OP) for example comprises from 80 to 94% by weight of the at least one extractant (E), from 4.5 to 12.5% by weight of water, from 0.7 to 3.2% by weight of byproducts, from 0.6 to 2.6% by weight of formaldehyde, and from 0.01 to 1% by weight of 1,3,5-trioxane, based on the sum of the percentage by weight of the least one extractant, water, the byproducts, formaldehyde and 1,3,5-trioxane comprised in the overhead product (OP), preferably based on the total weight of the overhead product (OP).

Preferably, the overhead product (OP) comprises from 84 to 92% by weight of the least one extractant (E), from 5.5 to 11.5% by weight of water, from 1.1 to 2.8% by weight of by products, from 1 to 2.2% by weight of formaldehyde, and from 0.05 to 0.8% by weight of 1,3,5-trioxane, based on the sum of the percentage by weight of the least one extractant (E), water, byproducts, formaldehyde and 1,3,5-trioxane comprised in the overhead product (OP), preferably based on the total weight of the overhead product (OP).

Particularly preferred, the overhead product (OP) comprises from 86 to 90% by weight of the least one extractant (E), from 6.5 to 10.5% by weight of water, from 1.5 to 2.4% by weight of byproducts, from 1.4 to 1.8% by weight of formaldehyde, and from 0.1 to 0.5% by weight of 1,3,5-trioxane, based on the sum of the percentage by weight of the least one extractant (E), water, byproducts, formaldehyde and 1,3,5-trioxane comprised in the overhead product (OP), preferably based on the total weight of the overhead product (OP).

The side cut (SC) which is obtained when the first product mixture (P1) is contacted with the at least one extractant (E) comprises the at least one extractant (E) and 1,3,5-trioxane.

For example, the side cut (SC) comprises from 10 to 20% by weight of the at least one extractant (E), from 15 to 40% by weight of 1,3,5-trioxane, from 20 to 40% by weight of formaldehyde and from 20 to 40% by weight of water, based on the sum of the percentage by weight of the at least one extractant (E), 1,3,5-trioxane, formaldehyde and water, preferably based on the total weight of the side cut (SC).

The percentages by weight of the at least one extractant (E), 1,3,5-trioxane, formaldehyde and water comprised in the side cut (SC) usually add up to 100%.

The side cut (SC) is withdrawn from the distillation tower (D) as stream (2a). This stream (2a) can be further purified to obtain 1,3,5-trioxane. Methods for purifying stream (2a) are known to the skilled person.

The side cut (SC) is usually withdrawn from the side of the distillation tower (D) as stream (2a).

In step b), the overhead product (OP) is then transferred as stream (2) from the distillation tower (D) to a mechanical compressor (MC). The stream (2) can be transferred from the distillation tower (D) to the mechanical compressor (MC) by any method known to the skilled person.

The overhead product (OP) usually exits from the top of the distillation tower (D) as stream (2).

As the overhead product (OP) is transferred as stream (2) from the distillation tower (D) to the mechanical compressor (MC), the stream (2) has the same composition as the overhead product (OP). Therefore, for the composition of the stream (2), the embodiments and preferences described above for the overhead product (OP) hold true.

Another object of the present invention is, therefore, a process wherein the stream (2) comprises from 80 to 94% by weight of the at least one extractant (E), from 4.5 to 12.5% by weight of water, from 0.7 to 3.2% by weight of byproducts, from 0.6 to 2.6% by weight of formaldehyde and from 0.01 to 1% by weight of 1,3,5-trioxane, based on the total weight of the stream (2).

The stream (2) has a first temperature (T1) and a first pressure (p1).

The first temperature (T1) of the stream (2) is usually in the range from 49 to 92° C., preferably in the range from 59 to 82° C., and particularly preferred in the range from 69 to 72° C.

Another object of the present invention is, therefore, a process wherein the first temperature (T1) of the stream (2) is in the range from 49 to 92° C.

The first pressure (p1) of the stream (2) is usually in the range from 0.05 to 2 bara, preferably in the range from 0.55 to 1.5 bara, and particularly preferred in the range from 0.95 to 1.2 bara.

Another object of the present invention is, therefore, a process wherein the first pressure (p1) of the stream (2) is in the range from 0.05 to 2 bara.

The stream (2) is usually gaseous.

As mechanical compressor (MC) to which the stream (2) is transferred, any mechanical compressor (MC) known to the skilled person is suitable.

The mechanical compressor (MC) is typically a turbo compressor. The mechanical compressor (MC) has multiple stages, typically from 2 to 6 stages and preferably from 3 to 4 stages. The mechanical compressor (MC) is preferably driven by a steam turbine or an electrical motor.

Step c)

In step c), the stream (2) is mechanically compressed in the mechanical compressor (MC) to obtain a compressed stream (3).

A mechanical compression is known to the skilled person. Usually, during the mechanical compression of the stream (2), the pressure and the temperature of the stream (2) are increased to obtain the compressed stream (3).

The obtained compressed stream (3) has the same composition as stream (2). Therefore, for the compressed stream (3), the embodiments and preferences concerning the composition of stream (2) hold true.

The compressed stream (3) has a second temperature (T2) and a second pressure (p2). The second temperature (T2) of the compressed stream (3) is higher than the first temperature (T1) of the stream (2). The second pressure (p2) of the compressed stream (3) is higher than the first pressure (p1) of the stream (2).

For example, the second temperature (T2) of the compressed stream (3) is in the range from 161 to 205° C., preferably in the range from 170 to 195° C., and particularly preferred in the range from 181 to 185° C.

Therefore, another object of the present invention is a process wherein the second temperature (T2) of the compressed stream (3) is in the range from 161 to 205° C.

Another object of the present invention is a process wherein the second temperature (T2) of the compressed stream (3) is higher than the first temperature (T1) of the stream (2).

The second pressure (p2) of the compressed stream (3) usually is in the range from 4 to 14 bara, preferably in the range from 6 to 12 bara, and particularly preferred in the range from 8 to 10 bara.

Another object of the present invention is, therefore, a process wherein the second pressure (p2) of the compressed stream (3) is in the range from 4 to 14 bara.

Another object of the present invention is a process wherein the second pressure (p2) of the compressed stream (3) is higher than the first pressure (p1) of the stream (2).

The compressed stream (3) is usually gaseous.

Step d)

In step d), heat is transferred from the compressed stream (3) to the first reactor (R1). The heat transfer from the compressed stream (3) to the first reactor (R1) can be carried out by all methods known to the skilled person. For example, the compressed stream (3) can be introduced into the first reactor (R1) or the compressed stream (3) can be transferred into at least one first heat exchanger (H1), wherein its heat can be transferred. This embodiment is preferred.

If the compressed stream (3) is introduced into the first reactor (R1) to transfer heat to the first reactor (R1), the compressed stream (3) can be introduced directly into the first reactor (R1). Moreover, it is possible that the compressed stream (3) is introduced into the wall, a heating jacket or a heating coil of the first reactor (R1) to heat the first reactor (R1).

As described above, it is preferred that the compressed stream (3) is transferred into at least one first heat exchanger (H1) to transfer heat to the first reactor (R1).

Another object of the present invention is, therefore, a process wherein in step d), the compressed stream (3) is transferred into at least one first heat exchanger (H1) to transfer heat to the first reactor (R1).

"At least one first heat exchanger (H1)" within the context of the present invention means precisely one first heat exchanger (H1) and also two or more first heat exchangers (H1). If two or more first heat exchangers (H1) are used, they can be arranged parallel or in series.

Particularly preferred, step d) comprises the following steps:
d1) transferring the compressed stream (3) from the mechanical compressor (MC) to a first heat exchanger (H1) in which heat is transferred from the compressed stream (3) to a condensate (C) in order to obtain a heated condensate (hC),
d2) transferring heat from the heated condensate (hC) to the first reactor (R1).

Another object of the present invention is, therefore, a process wherein step d) comprises the following steps
d1) transferring the compressed stream (3) from the mechanical compressor (MC) to a first heat exchanger (H1) in which heat is transferred from the compressed stream (3) to a condensate (C) in order to obtain a heated condensate (hC),
d2) transferring heat from the heated condensate (hC) to the first reactor (R1).

The compressed stream (3) can be transferred from the mechanical compressor (MC) to the first heat exchanger (H1) in step d1) by any method known to the skilled person.

Usually, the compressed stream (3) is transferred from the mechanical compressor (MC) to the first heat exchanger (H1) through a pipe.

As first heat exchanger (H1), any heat exchanger known to the skilled person is suitable. Preferred is a shell-and-tube heat exchanger. It is particularly preferred that the first heat exchanger (H1) is a shell-and-tube heat exchanger, wherein the compressed stream (3) is inside the tubes.

In the first heat exchanger (H1), heat is transferred from the compressed stream (3) to the condensate (C). The pressure of the condensate (C) usually is not altered during this heat transfer. The concept of heat transfer in a heat exchanger is known to the skilled person. Usually, the heat transfer from the compressed stream (3) to the condensate (C) in the first heat exchanger (H1) is carried out indirectly. "Indirectly" within the context of the heat transfer in the first heat exchanger (H1) means that the compressed stream (3) and the condensate (C) are not in direct contact but separated from each other, for example through a wall which is heat-permissible.

The condensate (C) usually has a temperature in the range from 60 to 120° C., preferably in the range from 70 to 110° C., and particularly preferred in the range from 80 to 100° C.

As condensate (C), any substance is suitable which is liquid or gaseous at the temperature and the pressure of the condensate (C) during the inventive process, and to which heat can be transferred. Preferably, the condensate (C) is liquid at the temperature and the pressure of the condensate (C) during the inventive process. It is furthermore preferred that the condensate (C) in step d1) comprises water. Particularly preferred, the condensate (C) in step d1) consists of water.

Another object of the present invention is, therefore, a process wherein the condensate (C) in step d1) comprises water.

During the heat transfer from the compressed stream (3) to the condensate (C), the temperature of the condensate (C) rises, whereas the pressure of the condensate (C) usually remains constant.

The condensate (C) usually is fed to the first heat exchanger (H1) as stream (4a). For the stream (4a), the embodiments and preferences described above for the condensate (C) hold true.

The heated condensate (hC) obtained in step d1) has the same composition as the condensate (C). Therefore, concerning the composition of the heated condensate (hC), the embodiments and preferences described above for the condensate (C) hold true.

As heat is transferred from the compressed stream (3) to the condensate (C) to obtain the heated condensate (hC), the temperature of the heated condensate (hC) is higher than the temperature of the condensate (C). During the heat transfer the condensate (C) is preferably partially or fully evaporated, particularly preferred fully evaporated. Therefore, the obtained heated condensate (hC) is usually gaseous.

Another object of the present invention is, therefore, a process wherein the temperature of the heated condensate (hC) is higher than the temperature of the condensate (C).

For example, the temperature of the heated condensate (hC) is in the range from 120 to 170° C., preferably in the range from 130 to 160° C., and particularly preferred in the range from 140 to 150° C.

The heated condensate (hC) is usually gaseous.

The compressed stream (3) transfers heat to the condensate (C) in step d1). During this heat transfer, the compressed stream (3) cools down and is transformed into a two-phase stream (3a). This two-phase stream (3a) is usually liquid and can be withdrawn from the first heat exchanger (H1).

The two-phase stream (3a) usually has a temperature in the range from 122 to 166° C., preferably in the range from 132 to 156° C., and particularly preferred in the range from 142 to 146° C.

The two-phase stream (3a) usually has a pressure in the range from 5 to 14 bara, preferably in the range from 7 to 12 bara, and particularly preferred in the range from 9 to 10 bara.

The two-phase stream (3a) can be purified by methods known to the skilled person and can then be recycled to the distillation tower (D). The recycling can be carried out by any method known to the skilled person.

In step d2), heat is transferred from the heated condensate (hC) to the first reactor (R1).

The transfer of the heat from the heated condensate (hC) to the first reactor (R1) can be carried out by any method known to the skilled person. For example, the heated condensate (hC) can be introduced into the first reactor (R1) or the heated condensate (hC) can be transferred into at least one second heat exchanger (H2). This embodiment is preferred.

If the heated condensate (hC) is introduced into the first reactor (R1) to transfer heat to the first reactor (R1), the heated condensate (hC) can be introduced directly into the first reactor (R1). Moreover, it is possible that the heated condensate (hC) is introduced into the wall, a heating jacket or a heating coil of the first reactor (R1) to heat the first reactor (R1).

As described above, it is preferred that the heated condensate (hC) is transferred into at least one second heat exchanger (H2) to transfer heat to the first reactor (R1).

Another object of the present invention is, therefore, a process wherein in step d2), the heated condensate (hC) is transferred into at least one second heat exchanger (H2) to transfer heat to the first reactor (R1).

"At least one second heat exchanger (H2)" within the context of the present invention means precisely one second heat exchanger (H2) and also two or more second heat exchangers (H2). If two or more second heat exchangers (H2) are used, they may be used in parallel or in series.

Particularly preferred, a second heat exchanger (H2) is used from which heat of the heated condensate (hC) is transferred to the first reactor (R1).

Therefore, preferably, step d2) comprises the following steps:
d2-i) transferring the heated condensate (hC) as stream (4) to a second heat exchanger (H2), in which heat is transferred from the stream (4) to a mixture (M) in order to obtain a heated mixture (hM), wherein the mixture (M) comprises formaldehyde and water,
d2-ii) transferring heat from the heated mixture (hM) to the first reactor (R1).

Another object of the present invention is, therefore, a process wherein step d2) comprises the following steps
d2-i) transferring the heated condensate (hC) as stream (4) to a second heat exchanger (H2), in which heat is transferred from the stream (4) to a mixture (M) in order to obtain a heated mixture (hM), wherein the mixture (M) comprises formaldehyde and water,
d2-ii) transferring heat from the heated mixture (hM) to the first reactor (R1).

In step d2-i), the heated condensate (hC) is transferred as stream (4) to a second heat exchanger (H2). For the stream (4), the embodiments and preferences described above for the heated condensate (hC) hold true.

Therefore, another object of the present invention is a process wherein the stream (4) has a temperature in the range from 120 to 170° C.

"A second heat exchanger (H2)" within the context of the present invention means precisely one second heat exchanger (H2) and also two or more second heat exchangers (H2). Two or more second heat exchangers (H2) are preferred. If two or more second heat exchangers (H2) are used, they can be used in parallel or in series, preferably they are used in parallel. To the person skilled in the art, it should be clear that if two or more second heat exchangers (H2) are used, then the stream (4) is split into two or more streams (4). Methods to split the stream (4) are known to the skilled person.

The mixture (M) to which heat is transferred from the stream (4) usually has a temperature in the range 80 to 140° C., preferably in the range from 90 to 130° C., and particularly preferred in the range 100 to 120° C.

The mixture (M) usually has a pressure in the range from 0.4 to 2.5 bara, preferably in the range from 0.8 to 2 bara, and particularly preferable in the range from 1.0 to 1.5 bara.

The mixture (M) is usually liquid.

The mixture (M) comprises formaldehyde and water. Any mixture (M) which comprises formaldehyde and water can be used. Preferably, the mixture (M) in step d2-i) is transferred as stream (5a) from the first reactor (R1) to the second heat exchanger (H2).

Another object of the present invention is, therefore, a process wherein the mixture (M) in step d2-i) is transferred as stream (5a) from the first reactor (R1) to the second heat exchanger (H2).

Therefore, the mixture (M) can comprise further components, in particular those components that are comprised in the first reactor (R1). These components are, for example, the at least one acidic catalyst, 1,3,5-trioxane and byproducts.

For the stream (5a), the embodiments and preferences described above for the mixture (M) hold true.

Heat is transferred from stream (4) to the mixture (M) to obtain the heated mixture (hM). During the heat transfer, the temperature of the mixture (M) is usually increased and the pressure of the mixture (M) remains constant. Usually, the heat transfer from the stream (4) to the mixture (M) in the second heat exchanger (H2) is carried out indirectly. "Indirectly" within the context of the heat transfer in the second heat exchanger (H2) means that the stream (4) and the mixture (M) are not in direct contact but separated from each other, for example through a wall which is heat-permissible.

The heated mixture (hM) has the same composition as the mixture (M). Therefore, for the composition of the heated mixture (hM), the embodiments and preferences concerning the composition of the mixture (M) hold true.

The heated mixture (hM) usually has a temperature in the range from 82 to 140° C., preferably in the range from 92 to 130° C., and particularly preferred in the range from 102 to 120° C.

The temperature of the heated mixture (hM) is usually higher than the temperature of the mixture (M).

Therefore, another object of the present invention is a process wherein the temperature of the heated mixture (hM) is higher than the temperature of the mixture (M).

The heated mixture (hM) usually has a pressure in the range from 0.4 to 2 bara, preferably in the range from 0.8 to 1.5 bara, and particularly preferable in the range from 1.0 to 1.5 bara.

The heated mixture (hM) is usually at least partially gaseous.

During the heat transfer from the stream (4) to the mixture (M), the stream (4) usually cools down and is transformed to a condensate (C). This condensate (C) can be withdrawn from the second heat exchanger (H2) as stream (4b) and can then be recycled to the first heat exchanger (H1).

The heated mixture (hM) transfers heat to the first reactor (R1) in step d2-ii). The heat transfer from the heated mixture (hM) to the first reactor (R1) can be carried out by any method known to the skilled person. Preferably, the heated mixture (hM) is transferred as stream (5b) from the second heat exchanger (H2) to the first reactor (R1) in step d2-ii).

Another object of the present invention is, therefore, a process wherein in step d2-ii) the heated mixture (hM) is transferred as stream (5b) from the second heat exchanger (H2) to the first reactor (R1).

For the stream (5b), the embodiments and preferences described above for the heated mixture (hM) hold true.

Therefore, another object of the present invention is a process wherein the stream (5b) has a temperature in the range from 82 to 140° C.

The inventive process makes it possible to recover energy from a process for the preparation of 1,3,5-trioxane. Moreover, most of the streams of the inventive process can at least partially be recycled which leads to a more cost-efficient process than the processes described in the state of the art.

A particularly preferred embodiment of the present invention will be described hereinafter with reference to FIG. 1.

In step a), formaldehyde is reacted in the presence of water and at least one acidic catalyst in the first reactor R1, and a first product mixture (P1) is obtained. The first product mixture (P1) comprises water and 1,3,5-trioxane, and is transferred as stream 1 from the first reactor R1 to a distillation tower D.

In the distillation tower D, the first product mixture (P1) is contacted with at least one extractant (E) in step b). An overhead product (OP) and a side cut (SC) are obtained. The side cut (SC) is withdrawn as stream 2a from the side of the distillation tower D. The side cut (SC) comprises the at least one extractant (E) and 1,3,5-trioxane.

The overhead product (OP) exits the top of the distillation tower D as stream 2. The overhead product (OP) comprises the at least one extractant (E) and water. In step b), the overhead product (OP) is transferred as stream 2 from the distillation tower D to a mechanical compressor MC. In the mechanical compressor MC, the stream 2 is mechanically compressed in step c) to obtain the compressed stream 3. The compressed stream 3 has a second temperature (T2) which is higher than the first temperature (T1) of the stream 2. Furthermore, the compressed stream 3 has a second pressure (p2) which is higher than the first pressure (p1) of the stream 2.

The obtained compressed stream 3 is transferred in step d1) from the mechanical compressor MC to a first heat exchanger H1. In the first heat exchanger H1, heat is transferred from the compressed stream 3 to a condensate (C) in order to obtain a heated condensate (hC). The condensate (C) is added as stream 4a to the first heat exchanger H1.

During the heat transfer from the compressed stream 3 to the condensate (C), the compressed stream 3 cools down and condenses to give a two-phase stream 3a which is withdrawn from the first heat exchanger H1.

The heated condensate (hC) is transferred as stream 4 to a second heat exchanger H2 in step d2-i). In the second heat exchanger H2, the stream 4 transfers heat to a mixture (M) to obtain a heated mixture (hM). The mixture (M) is transferred from the first reactor R1 as stream 5a to the second heat exchanger H2.

The heated mixture (hM) obtained in step d2-i) is then transferred as stream 5b to the first reactor R1. During the transfer of heat from the stream 4 to the mixture (M), the stream 4 cools down and a condensate (C) is obtained which can be withdrawn from the second heat exchanger H2 as stream 4b.

The examples below illustrate, but do not restrict the invention.

EXAMPLE 1

Example 1 is an example according to the invention. The process for energy recovery in a process for the preparation of 1,3,5-trioxane is carried out according to the preferred embodiment described above with reference to FIG. 1. The process is carried out continuously. In the first reactor (R1), 61.9% by weight of formaldehyde are reacted in the presence of 34.8% by weight of water and 3.5% by weight of sulfuric acid. The first reactor (R1) is operated at a temperature of 107° C. and a pressure of 1.4 bara (bar absolute).

During the reaction in the first reactor (R1), formaldehyde trimerizes in the presence of water and sulfuric acid to give 1,3,5-trioxane. From the first reactor (R1), the first product mixture (P1) is transferred as stream (1) to the distillation tower (D).

The distillation tower (D) comprises a distillation section, an extraction section, a side discharge and an overhead discharge. The distillation tower is a tray column. The distillation section is located underneath the side discharge of the distillation tower (D). The extraction section is located above the side discharge of the distillation tower (D). The stream (1) is transferred to the bottom of the distillation section of the distillation tower (D). Benzene is used as an extractant. The extractant is fed to the top of the extraction section of the distillation tower (D). The temperature in the lowest tray of the distillation tower (D) is 105° C., the pressure is 1,4 bara. The temperature at the head of the distillation tower (D) is held at 71° C., the pressure is 1.1 bara.

From the side discharge, the side cut (SC) is discharged as stream (2a). The side cut (SC) comprises 18.7% by weight of benzene, 28.6% by weight of 1,3,5-trioxane, 27.3% by weight of formaldehyde and 25.4% by weight of water. From the overhead discharge of the distillation tower (D), the overhead product (OP) is discharged as stream (2). The overhead product (OP) comprises 88% by weight of benzene, 8.0% by weight of water, 2.1% by weight of by-products, 1.6% by weight of formaldehyde and 0.3% by weight of 1,3,5-trioxane. Stream (2) has a pressure of 1.1 bara and a temperature of 71° C.

Stream (2) is transferred to the mechanical compressor (MC), which is a turbocompressor having three stages, driven by an electrical motor. In the mechanical compressor (MC), stream (2) is compressed. From the mechanical compressor (MC), the compressed stream (3) is discharged. The compressed stream (3) has a pressure of 9 bara and a temperature of 181° C. The compressed stream (3) is transferred to the first heat exchanger (H1). The heat of the compressed stream (3) is transferred to the condensate (C), which is fed as stream (4a) to the first heat exchanger (H1). The condensate (C) is heated in the first heat exchanger (H1) to obtain the heated condensate (HC), which is discharged as stream (4) from the first heat exchanger (H1) in order to transfer heat to the first reactor (R1). The heated condensate ((hC); stream (4)) has a temperature of 136° C.

In inventive example 1, in one hour one ton of 1,3,5-trioxane is produced. In order to produce one ton of 1,3,5-trioxane in one hour, according to inventive example 1, 4.56 tons per hour steam (pressure stage 3.2 bar; energy equivalent 2.53 MW are needed.

COMPARATIVE EXAMPLE 2

Comparative example 2 is carried out in the same way as the inventive example 1 described above, with the difference that the overhead product (OP) discharged as stream (2)

from the distillation tower (D) is not transferred to the mechanical compressor (MC). In other words, the process according to the comparative example 2 is run without mechanical vapor compression, but otherwise identical to inventive example 1. By consequence, stream (2) cannot be used to transfer heat to the condensate (C) and, therefore, no heated condensate (hC) can be obtained in order to transfer heat to the first reactor (R1). In comparative example 2, in one hour one ton of 1,3,5-trioxane is produced. In order to produce one ton of 1,3,5-trioxane in one hour, according to comparative example 2, 22 tons per hour steam (pressure stage 3.2 bara; energy equivalent 12.22 MW are needed.

The invention claimed is:

1. A process for energy recovery in a process for the preparation of 1,3,5-trioxane comprising the steps
    a) reacting formaldehyde in the presence of water and at least one acidic catalyst in a first reactor to obtain a first product mixture, which comprises water and 1,3,5-trioxane, wherein the first product mixture is transferred as a first stream from the first reactor to a distillation tower,
    b) contacting the first product mixture with at least one extractant in the distillation tower to obtain an overhead product, and a side cut, wherein the overhead product comprises the at least one extractant and water, and wherein the side cut comprises the at least one extractant and 1,3,5-trioxane, wherein the overhead product is transferred as a second stream from the distillation tower to a mechanical compressor, wherein the second stream has a first temperature and a first pressure,
    c) mechanical compression of the second stream in the mechanical compressor to obtain a compressed stream, which has a second temperature and a second pressure, wherein the second temperature of the compressed stream is higher than the first temperature of the second stream and wherein the second pressure of the compressed stream is higher than the first pressure of the second stream,
    d) transferring heat from the compressed stream to the first reactor.

2. The process according to claim 1, wherein step d) comprises the following steps
    d1) transferring the compressed stream from the mechanical compressor to a first heat exchanger in which heat is transferred from the compressed stream to a condensate in order to obtain a heated condensate,
    d2) transferring heat from the heated condensate to the first reactor.

3. The process according to claim 2, wherein step d2) comprises the following steps
    d2-i) transferring the heated condensate as a fourth stream to a second heat exchanger, in which heat is transferred from the fourth stream to a mixture in order to obtain a heated mixture, wherein the mixture comprises formaldehyde and water,
    d2-ii) transferring heat from the heated mixture to the first reactor.

4. The process according to claim 3, wherein the mixture in step d2-i) is transferred as a stream 5a from the first reactor to the second heat exchanger.

5. The process according to claim 3, wherein in step d2-ii) the heated mixture is transferred as a stream 5b from the second heat exchanger to the first reactor.

6. The process according to claim 1, wherein the at least one extractant in step b) is selected from the group consisting of benzene, 1,2-dichloroethane and methylene chloride.

7. The process according to claim 1, wherein the first stream in step a) comprises from 31 to 56% by weight of formaldehyde, from 8 to 32% by weight of 1,3,5-trioxane, from 11 to 35% by weight of water and from 1 to 25% by weight of byproducts, based on the total weight of the first stream.

8. The process according to claim 1, wherein the first temperature of the second stream is in the range from 49 to 92° C.

9. The process according to claim 1, wherein the first pressure of the second stream is in the range from 0.05 to 2 bara.

10. The process according to claim 1, wherein the second temperature of the compressed stream is in the range from 161 to 205° C.

11. The process according to claim 1, wherein the second pressure of the compressed stream is in the range from 4 to 14 bara.

12. The process according to claim 1, wherein the second stream comprises from 80 to 94% by weight of the at least one extractant, from 4.5 to 12.5% by weight of water, from 0.7 to 3.2% by weight of byproducts, from 0.6 to 2.6% by weight of formaldehyde and from 0.01 to 1% by weight of 1,3,5-trioxane, based on the total weight of the second stream.

13. The process according to claim 2, wherein the condensate in step d1) comprises water.

14. The process according to claim 3, wherein the fourth stream has a temperature in the range from 120 to 170° C.

15. The process according to claim 5, wherein the stream 5b has a temperature in the range from 82 to 140° C.

* * * * *